(12) United States Patent
Kung-Ming

(10) Patent No.: US 6,685,973 B1
(45) Date of Patent: Feb. 3, 2004

(54) **METHOD FOR INHIBITING 15-LIPOXYGENASE WITH FERMENTED *GLYCINE MAX* (L.) EXTRACT**

(75) Inventor: William Lu Kung-Ming, Taipei (TW)

(73) Assignee: Microbio Company, Ltd., Taiwan (TW)

( * ) Notice: Subject to any disclaimer, the term of this patent is extended or adjusted under 35 U.S.C. 154(b) by 0 days.

(21) Appl. No.: 10/125,336

(22) Filed: Apr. 17, 2002

Related U.S. Application Data

(63) Continuation-in-part of application No. 09/812,579, filed on Mar. 21, 2001, now abandoned.

(51) Int. Cl.$^7$ .............................................. A01N 65/00
(52) U.S. Cl. ....................................................... 424/757
(58) Field of Search ................................ 424/757, 93.3, 424/93.4, 93.45, 93.51; 514/824, 826, 885

(56) References Cited

U.S. PATENT DOCUMENTS

| | | | |
|---|---|---|---|
| 4,847,099 A | * | 7/1989 | Elinsky |
| 5,972,394 A | * | 10/1999 | Kato et al. |
| 6,001,866 A | | 12/1999 | Cornicelli et al. |
| 6,303,161 B1 | * | 10/2001 | Takebe et al. |

FOREIGN PATENT DOCUMENTS

| | | | |
|---|---|---|---|
| EP | 896797 | * | 2/1999 |
| JP | 10210947 | * | 8/1998 |
| JP | 10229841 | * | 9/1998 |
| JP | 20000004868 | * | 1/2000 |

OTHER PUBLICATIONS

J. Clin. Invest. 1996, vol. 98, No. 10, pp. 2201–2208.
American Heart Association, Inc. 1995, vol. 92 (11), pp. 3297–3303.
Arteriosclerosis, Thrombosis and Vascular Biology, 1995, vol. 15, No. 3, pp. 340–348.
J. Clin. Invest., 1997, vol. 99, No. 5, pp. 888–893.
Biochemistry, 2001, 40, 4391–4397.
Molecular Pharmacology, 1999, 56: 196–203.
The Journal of Biological Chemistry, 1998, vol. 273, No. 34, pp. 21569–21577.
Clin Exp Immunol, 2001, 126:2–8.

* cited by examiner

*Primary Examiner*—Christopher R. Tate
(74) *Attorney, Agent, or Firm*—LaRiviere, Grubman & Payne, LLP

(57) ABSTRACT

This invention relates to a use of a fermented *Glycine max* (L.) extract prepared by fermenting an aqueous *Glycine max* (L.) extract with at least one lactic acid bacteria together with at least one yeast, in inhibiting 15-lipoxygenase. In particular, the fermented *Glycine max* (L.) extract can be used in preventing and/or treating a disease in which 15-lipoxygenase inhibition is implicated in a subject, such as cardiovascular diseases, cancer, immune disorders, such as asthma, and inflammation and modulating the immune system. The invention also relates to a use of the fermented *Glycine max* (L.) extract in treating and/or preventing a microbe infection.

5 Claims, 14 Drawing Sheets

■ Control
□ FSE 0.80 mg/ml
▨ FSE 1.60 mg/ml
▨ FSE 0.24 mg/ml
▩ FSE 0.32 mg/ml
≡ FSE 0.80 mg/ml
∥∥ FSE 0.16 mg/ml
▓ FSE 3.20 mg/ml

METHOD FOR INHIBITING 15-LIPOXYGENASE WITH FERMENTED *GLYCINE MAX* (L.) EXTRACT

RELATED APPLICATION(S)

The present application is a continuation in part application of U.S. patent application Ser. No. 09/812,579, filed on Mar. 21, 2001, now abandoned.

TECHNICAL FIELD

This invention relates to a use of a fermented *Glycine max* (L.) extract in inhibiting 15-lipoxygenase, preventing and/or treating a disease in which 15-lipoxygenase inhibition is implicated in a subject, such as cardiovascular diseases, cancer, immune disorders, such as asthma and or inflammation, and modulating the immune system. The invention also relates to a use of the fermented *Glycine max* (L.) extract in preventing and/or treating a microbe infection.

BACKGROUND OF THE INVENTION

Lipoxygenases (LOX) are nonheme iron-containing enzyme that catalyze the oxygenation of certain polyunsaturated fatty acids such as lipoproteins. Several different lipoxygenase enzymes, e.g. LOX-5, LOX-12 and LOX-15, are known, each having a characteristic oxidation action. LOX-15 catalyzes the oxygenation of arachidonic and linoleic acids and has been implicated in the oxidative modification of low-density lipoproteins (LDL). Many researches reported that the LOX-15 is associated with coronary artery disease and atherosclerosis (Shen et al., J. Clin. Invest. 1996, Vol. 98, No. 10, pp. 2201–2208; Timo et al., 1995, Vol. 92 (11), pp. 3297–3303; Ravalli et al., 1995, Arteriosclerosis, Thrombosis and Vascular Biology, Vol. 15, No. 3, pp. 340–348; and Kuhn et al., 1997, J. Clin. Invest., Vol. 99, No. 5, pp. 888–893), cancer and inflammatory diseases Molecular Pharmacology, 56: 196–203; and Kamitani et al., 1998, the Journal of Biological Chemistry, Vol. 273, No. 34, pp. 21569–21577), and immune response (Kruisselbrink et al., 2001, Clin Exp Immunol, 126:2–8). Therefore, a substance having an efficacy in inhibiting LOX is useful as an agent for preventing or treating diseases associated with LOX.

Soybeans are one concentrated source of isoflavones in human diet. They also contain many compounds including saponins, phytosterols, soybean phytates, protease inhibitors, phenolic acids, complex sugars, boron, lecithin, omega-3 fatty acids and folic acid. They can impart health benefits. Many eastern traditional foods, such as tembe and natto, are produced from the fermentation of soybeans. For example, tembe is produced by fermenting soybean with *Rhizopus oligosporus, R. oryzae, R. arrihizus and R. stolonifer*. Natto is produced by fermenting soybean with *Bacillus natto*. The traditional fermented foods can be used as a superior protein origin. However, none of the prior art discloses that any known fermented soybean foods and soybeans have an efficacy in inhibiting 15-lipoxygenase LOX-15.

SUMMARY OF THE INVENTION

This invention relates to a use of a fermented *Glycine max* (L.) extract, which is prepared by fermenting an aqueous *Glycine max* (L.) extract with at least one lactic acid bacteria together with at least one yeast, in inhibiting 15-lipoxygenase (LOX-15).

One objective of the invention is to provide a method of inhibiting 15-lipoxygenase in a subject, comprising administering an effective amount of a fermented *Glycine max* (L.) extract to the subject in need of thereof, wherein the fermented *Glycine max* (L.) extract is prepared by fermenting an aqueous *Glycine max* (L.) extract with at least one lactic acid bacteria together with at least one yeast. Particularly, *Glycine max* (L.) is soybean or black soybean. More particularly, the fermented *Glycine max* (L.) extract of the invention include the fermented soybean extract and fermented black soybean extract.

Another objective of the invention is to provide a method of preventing and/or treating a disease in which 15-lipoxygenase (LOX-15) inhibition is implicated in a subject, comprising administering an effective amount of the fermented *Glycine max* (L.) extract to the subject in need of thereof. In particular, the fermented *Glycine max* (L.) extract of the invention can be used in preventing and/or treating a disease in which 15-lipoxygenase inhibition is implicated in a subject, such as cardiovascular diseases, cancer, immune disorders, such as asthma, inflammation, and modulating the immune system.

A further objective of the invention also relates to a method for preventing and/or treating a microbe infection in a subject, comprising administering an effective amount of the fermented *Glycine max* (L.) extract of the invention.

BRIEF DESCRIPTION OF THE DRAWINGS

FIG. 3 shows the antioxidant effect of gallic acid. At a temperature of 37° C., chemiluminescence, CL Counts, was measured after the addition of $H_2O_2$ as a peroxide (X), gallic acid as an antioxidant (Y) and/or acetaldehyde as a radical receptor (Z).

FIG. 4 shows the antioxidant effects of tea and Vitamin C. At a temperature of 37° C., chemiluminescence, in CL Counts, was measured in the presence of $H_2O_2$ as a peroxide with the presence or absence acetaldehyde (Z) as a radical receptor, and an addition of one of several antioxidants, i.e. EGC, tea and vitamin C, at 200 seconds.

FIG. 6 shows the time course and dose response of FSE on a human breast cancer cell line, MCF-7 cells. MCF-7 cells ($5 \times 10^4$/ell) were treated with indicated doses of FSE for 24–96 hours and the viability of the MCF-7 cells was measured by an MTT assay.

FIG. 7 shows that FSE could induce apoptotic cell death. Under a treatment of MCF-7 cells with FSE at a concentration of 1.6 mg/ml, the DNA fragmentation pattern was characterized by electrophoresis on 2.0% agarose gel and was further quantitated by TUNEL assay.

DETAILED DESCRIPTION OF THE INVENTION

Figure 1:
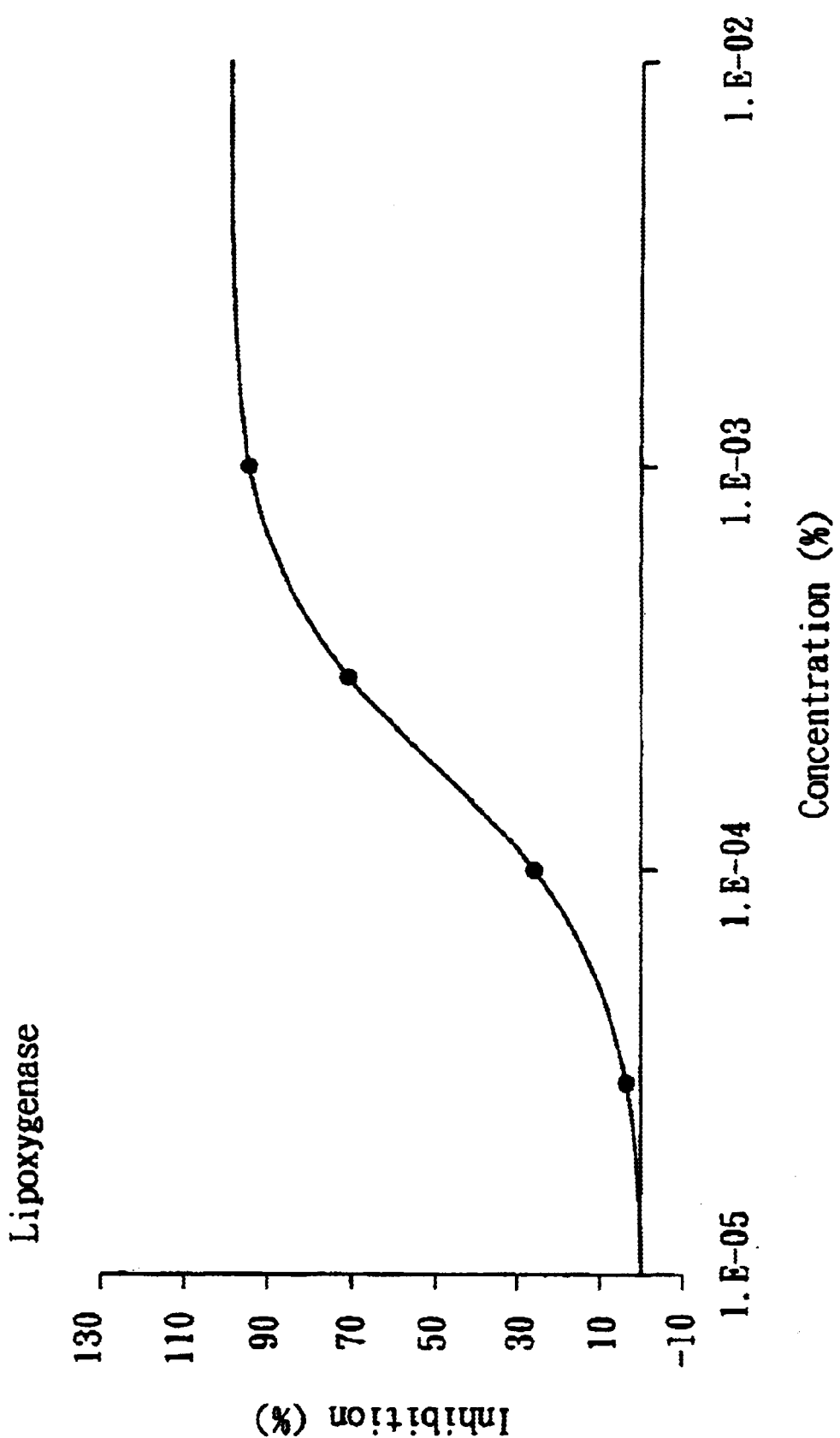
FIG. 1 shows the inhibition of LOX-15 with the fermented soybean extract.

The invention relates to a new use of a fermented *Glycine max* (L.) extract in the inhibition of 15-lipoxygenase (LOX-15) and the diseases implicated in the 15-lipoxygenase, wherein the fermented *Glycine max* (L.) extract is prepared by fermenting an aqueous *Glycine max* (L.) extract with at least one lactic acid bacteria together with at least one yeast. It is unexpectedly found that the fermented *Glycine max* (L.) extract can effectively inhibit 15-lipoxygenase in a low level.

In particular, the fermented *Glycine max* (L.) extract of the invention can be used in preventing and/or treating a disease in which 15-lipoxygenase inhibition is implicated in a subject, such as cardiovascular diseases, cancer, immune disorders, such as asthma, inflammation, and modulating the immune system. In addition, the fermented soybean extract of the invention can also be used in treating and/or preventing a microbe infection. Process for Producing the Fermented Soybean Extract The fermented *Glycine max* (L.) extract is made by fermentation of an aqueous *Glycine max* (L.) extract with at least one lactic acid bacteria together with at least one yeast, followed by sterilization, e.g. by heat, of the fermented liquid with optional filtration and concentration.

According to the invention, the preferred *Glycine max* (L.) used in the preparation of the fermented *Glycine max* (L.) extract is selected from the group consisting of soybean and black soybean. More particularly, the fermented *Glycine max* (L.) extract of the invention is the fermented soybean extract or fermented black soybean extract.

The fermented *Glycine max* (L.) extract is produced by fermentation of *Glycine max* (L.) extract with at least one lactic acid bacteria, e.g. one or more strains of a Lactobacillus species or several strains of a number of Lactobacillus species, together with at least one yeast, e.g. one or more strains of a Saccharomyces species or several strains of a number of Saccharomyces species. The fermentation of the aqueous *Glycine max* (L.) extract with one or more lactic acid bacteria and the optional Saccharomyces species can be carried out sequentially in any order or simultaneously, preferably simultaneously.

If more than one microbe is used in the fermentation, the fermentation can be conducted with the microbes sequentially or simultaneously. Preferably, an aqueous extract of non-genetically modified organic *Glycine max* (L.) of selected grade is used as a starting material. Preferably, the fermentation is carried out using a heterogeneous culture of Lactobacillus, for example, a culture of 5, 10, 15, 20, 25 or 30 strains of Lactobacillus and at least one yeast is added to the heterogeneous culture of Lactobacillus. The strains of Lactobacillus that can be used include, for examples, *Lactobacillus acidophilus* CCRC 10695, 14026, 14064, 14065 and/or 14079, *Lactobacillus delbrueckii bulgaricus* CCRC 10696, 14007, 14009, 14010, 14069, 14071, 14098 and/or 16054, *Lactobacillus lactis lactis* CCRC 10791, 12267, 12306, 12312, 12315, 12323, 14016, 14015 and/or 14117, *Lactobacillus kefyir* CCRC 14011, and/or *Lactobacillus kefiranofaciens* CCRC 16059. The yeast that can be used include, for example, *Saccharomyces cerevisiae* CCRC 20577, 20578, 20581, 21494, 21550, 21797, 21805, 22138, 22234, 22337, 22731 and/or 22728, and/or *Candida kefyr* CCRC 21269, 21742 and/or 22057. After fermentation, the fermented liquid is sterilized, e.g. by heat or irradiation, preferably by heat, to obtain a sterilized liquid. Preferably, the sterilized liquid is filtered or centrifuged, preferably filtered, to remove most or all of the dead microbes to obtain the fermented *Glycine max* (L.) extract. More preferably, the filtration step is followed by removal of some of the water from the filtrate to concentrate the fermented liquid to obtain the fermented *Glycine max* (L.) extract. Unless otherwise specified, the tests performed in this application involved the fermented *Glycine max* (L.) extract after the concentration step. Optionally, the fermented *Glycine max* (L.) extract can be dried, e.g. via lyophilization, to obtain the fermented *Glycine max* (L.) extract in a powder form.

The process can be carried out by mixing organic *Glycine max* (L.) (with fat removed) with distilled water at a ratio of 1:10. The mixture is heated at 100° C. for 30 minutes and then filtered to obtain a *Glycine max* (L.) extract. Beef and kelp are boiled in distilled water for 30 minutes to obtain a broth. Salt, sugar and agar are added to produce a special agar medium. The lactic acid bacteria and yeast strains are added to the special agar medium. The lactic acid bacteria with the optional inclusion of the yeast in the medium are transferred to the *Glycine max* (L.) extract and incubated at 36–43° C. for 45–50 hours. Preferably, the various strains of the microbes are grouped according to similar growth characteristics, e.g. any requirements of unique nutrient medium, whether the microbial strains could produce a good smell after fermentation and whether the grouped microbes can survive in the unique condition, so that groups of the microbes are added to the *Glycine max* (L.) extract separately before the incubation. The purpose of this step is to reduce any negative interaction among the various strains. Also preferably, equal proportion of the different groups of microbial strains are added to the *Glycine max* (L.) extract before the incubation and the resulting extract is incubated at 40° C. for 45–47 hours. Upon completion of the incubation period, the heterogeneous culture is then transferred to the *Glycine max* (L.) extract again and incubated at 36–43° C. for 100–150 hours. The final fermented extract is heat sterilized and filtered; and 95% of the water content of the filtrate is removed in a concentrator to obtain a fermented *Glycine max* (L.) extract in a concentrated or condensed form. The upper layer is then filtered through porcelain, and thereafter dispensed in containers and sealed.

Within the scope of the present invention is a fermented extract of a Chinese herb prepared in a process similar to the one described above with the substitution of the soybean with the Chinese herb. The fermented extract of the Chinese herbs can be *Glycyrrhiza uralensis* Fish, *Lycium barbarum*, *Coix lacryma-jobi* L var., ma-yune Stapf; *Sophora tonkinensis* gapnep., *Cassia btusifolia.*, *Scutellaria baicalensis* Georgi, *Artemisia capillaries* Thunb., *Coptis chinensis* Frsnch., *Gentiana scabra* Bge., *Nelumbo nucifera* Gaertn., *Chrysantheiferamum morifolium* Ramat., *Gardenia jasminoides* Ellis, *Hordeum vulgare* L., *Cinnamomum cassia* Presl, Raph, *anus sativus* L., *Dioscorea opposita* Thunb., *Angelica sinensis* (Oliv.), *Ligusticum chuanxiong* Hort., *Notopterygium incisum, Paeonia lactiflora* Pall., *Allium satium* L., *Schisandra chinensis*(Turcz.)Baill, *Rehmannia glutinosa* Libosch., *Acanthopanax gracilistylus* W. W. Smith, *Equus asinus* L., *Ligustrum lucidum* Ait., *Phaseolus radiatus* L., *Triticum aestivum* L., *Dolichos lablab* L., *Atractylodes macrocephala* Koidz., *Saposhnikovia divaricata, Lonicera japonica* Thund., *Cinnamomum cassia* Presl, *Zingiber officinale* Rosc., *Gastrodia elata* Bl., *Asparagus cochinchinensis*(Liur.)Merr., *Dendrobiun loddigesii* Rolfe., and *Sesamum indicum* L.

Use in the Inhibition of 15-lipoxygenase 15-lipoxygenases are nonheme iron-containing enzymes that catalyze the oxygenation of certain polyunsaturated fatty acids such as lipoproteins. It is known that compounds inhibit the action of 15-lipoxygenase enzyme are useful in the treatment or alleviation of cancer, inflammatory diseases, allergy, cardiovascular diseases and immune disorders in mammals including humans.

Studies in the invention have demonstrated that the fermented *Glycine max* (L.) extract can inhibit 15-lipoxygenases superior than known fermented soybean foods and unfermented soybean. The 15-lipoxygenases are highly expressed in most of malignant cancer cells such as prostate cancer cells, breast cancer cells and epithelial cancer cells (Shappell et al., Cancer Research, 61, 497–503, Jan. 15, 2001; Reddy et al., Biochemical and Biophysioal Research Communications, 281, 111–116, 1997; and Hong et al., Cancer Research, 59, 2223–2228, May 1, 1999). The inhibition of 15-lipoxygenases by the fermented *Glycine max* (L.) extract can have antiproliferative effects by modulating signal transduction, modulating growth factor activation and inhibiting oncogene expression.

The inhibition of 15-lipoxygenases by the fermented *Glycine max* (L.) extract can also induce apoptosis. The induction of apoptosis by the fermented *Glycine max* (L.) extract can be due to the anti-oxidant activity of the fermented *Glycine max* (L.) extract. The inhibition of 15-lipoxygenases by the fermented *Glycine max* (L.) extract can also inhibit angiogenesis resulting in inhibition of membrane degradation, decreased tumor cell adhesion and motility, and inhibition of metastasis. The inhibition of 15-lipoxygenases by the fermented *Glycine max* (L.) extract can also result in anti-inflammatory activities leading so that the fermented *Glycine max* (L.) extract can prevent tissue damage. With the inhibition of 15-lipoxygenase the fermented *Glycine max* (L.) extract is useful in preventing or treating cancer, asthma, coronary heart disease, cardiac failure, inflammation, allergy, ulcerative colitis, pruritis and dermatitis, and also useful in immunomodulation.

Arachidonic acid (AA) is an essential component of the cell membrane phospholipids, and LOX-15 is the main metabolizing enzyme in AA (Arachidonic acid) metabolism. AA metabolism can result in the generation of mutagens capable of damaging DNA and inducing mutations. AA is metabolized via two major biochemical pathways: (i) the cyclooxygenase (COX) pathway leading to the generation of prostaglandins (ii) the 15-lipoxygenase (LOX-15) pathway leading the generation of hydroxy (HETEs) fatty acids. HETEs have been reported to play a significant role in cancer cell metastasis, induction of protein kinase C activity, and angiogenesis. Therefore the reduced synthesis of LOX-15 can result in suppression of tumor growth. In addition, many studies shows that the inhibitors of LOX-15 are associated with atherosclerosis.

Given the above, the fermented *Glycine max* (L.) extract of the invention has the superior effects on the inhibition of 15-lipoxygenase and thus can be used in preventing and/or treating a disease in which 15-lipoxygenase inhibition is implicated in a subject, such as cardiovascular diseases, cancer, immune disorders, such as asthma, inflammation and modulating the immune system. In an embodiment of the invention, the fermented *Glycine max* (L.) extract can be used as an antioxidant, an anti-inflammation agent, an anti-cancer agent, an agent for promoting immune function, an anti-allergy agent, or an agent for treating cardiovascular diseases.

Use as an Antioxidant

The fermented *Glycine max* (L.) extract has prominent antioxidant and free radical scavenger activities. The fermented *Glycine max* (L.) extract can remove superoxide free radicals, e.g. $O_2$—$H_2O_2$, ROO, and can act as an antioxidant for unsaturated fatty acid and fat. The fermented *Glycine max* (L.) extract has a prominent ability to eliminate hyper oxygen anions to protect the cell from oxidative injury and change free radicals to harmless substances with an energy decreasing procedure.

Use as Agent Against Cardiovascular Diseases

Many studies shows that the inhibitors of LOX-15 in the treatment and prevention of inflammation and atherosclerosis (Cornicelli et al., U.S. Pat. No. 6,001,866; Bocan et al, Atherosclerosis, 136, 203–216, 1998 and Timo et al., Circulation, col. 92 (1), Dec. 1, 1995, pp. 3297–3303). It is expected that the fermented *Glycine max* (L.) extract is useful for preventing and/or treating cardiovascular diseases, such as atherosclearosis.

Use for Promoting Immune Function

In vitro study indicated that the fermented *Glycine max* (L.) extract of the invention improved immune function. The effect of the fermented *Glycine max* (L.) extract on modulation of the immunity of animals (Bala/c mice) was studied by treating the animal with the fermented *Glycine max* (L.) extract combined with or without a challenge with various mitogens including lipopolysachrride, concanavalin A and phytohaemagglutilin. Spleen cell proliferation assay indicated that the fermented *Glycine max* (L.) extract could be related with T & B cell interaction in immunity modulation. The fermented *Glycine max* (L.) extract can also be correlated with anti-inflammation reaction. The *Glycine max* (L.) extract also enhanced phagocytosis activity of macrophages by 71%. Similar results were found with in vivo studies in mice. It was also demonstrated that the anti-tumor effect of fermented *Glycine max* (L.) extract is mediated by cytokines released. Conditioned medium from fermented *Glycine max* (L.) extract-stimulated peripheral blood mononuclear cells by 45–56%. Levels of interleukin-1b, interleukin-b and tumor necrosis factor-a were much higher than those of untreated control. Since untreated Macrophages and T Lymphocytes produced little or no cytokine and normal mononuclear cells did not suppress leukemic cell growth, the anti-tumor activity is speculated to be derived from elevated level of cytokine.

The fermented *Glycine max* (L.) extract is beneficial to asthmatic children. For example, results obtained also showed significant body weight gain in a group of children with asthma when administered with 3 ml of the fermented soybean extract daily for 4 months. Blood tests showed that taking fermented *Glycine max* (L.) extract increase the RBC and Hb levels in these asthmatic children.

Use as Anti-cancer Agent

The fermented *Glycine max* (L.) extract of the present invention has anti-cancer activity for the treatment and/or prevention of cancer, whilst overcoming one or more disadvantages of prior art chemotherapeutic agents available for the treatment cancer. The cancer that can be treated with the fermented *Glycine max* (L.) extract includes the most prevalent types of cancer in the human population, namely breast cancer, colon cancer, cervix, prostate, kidney, lung, colon and liver cancers.

In cancer cells, the fermented *Glycine max* (L.) extract of the present invention can induce one or more effects of inhibition of cell proliferation, induction of cell differentiation, induction of apoptosis (programmed cell death), and/or cell cycle blocking. As a consequence, the extract of the present invention have wide ranging activity against cancer cells and are accordingly effective in the treatment and/or prevention of cancers including benign prostatic hypertrophy, prostatic cancer, breast cancer, uterine cancer, leukemia, ovarian cancer, endometrial cancer, cervical cancer, colon cancer, testicular cancer, lymphoma, rhabdosarcoma, neuroblastoma, pancreatic cancer, lung cancer, brain tumor, skin cancer, gastric cancer, oral cancer, liver cancer, laryngeal cancer, bladder cancer, thyroid cancer, liver cancer, kidney cancer and nasoharyngeal carcinoma.

Use as Anti-inflammation Agent

The invention also relates to a method for treating and/or preventing inflammation in a subject, comprising administering an effective amount of a fermented *Glycine max* (L.) extract to the subject in need of thereof, wherein the fermented *Glycine max* (L.) extract is prepared by fermenting an aqueous *Glycine max* (L.) extract with at least one lactic acid bacteria together with at least one yeast.

The fermented *Glycine max* (L.) extract has demonstrated anti-inflammatory effect at dosage of 10 ml/kg on the reduction of carrageenan induced hind paw edema in rats and anti-inflammatory effect on acute and chronic arthritis in adjuvant arthritis test.

Use for Preventing or Treating Infections

The fermented *Glycine max* (L.) extract has demonstrated antimicrobial activity in vitro and in vivo. It inhibits the growth of *Helicobacter pylori*, ampicillin and methycillin resistant *Staphylococcus aureus, Salmonella typhimurium, Bacillus subtilis, E.coli, Proteus vulgaris* and Vancomycin resistant Enterococci. Preferably, the Vancomycin resistant Enterococcus is selected from the group consisting of *E. avium, E. casseliflavus, E. durans, E. faecalis* and *E. faecium*. More Preferably, the Vancomycin resistant Enterococcus is selected from the group consisting of *E. avium, E. casseliflavus, E. durans* and *E. faecali*. More Preferably, the Vancomycin resistant Enterococcus is selected from the group consisting of *E. durans, E. faecalis* and *E. faecium*. More Preferably, the Vancomycin resistant Enterococcus is selected from the group consisting of *E. avium, E. faecalis* and *E. faecium*. More Preferably, the Vancomycin resistant Enterococcus is selected from the group consisting of *E. faecalis* and *E. faecium*. Most preferably, the Vancomycin resistant Enterococcus is *E. faecalis*.

The effective concentration of fermented *Glycine max* (L.) extract is generally in the range of 1–10%. The selective antimicrobial decontamination effect of fermented *Glycine max* (L.) extract for prophylaxis of bacterial infection in patients who are under risk of developing neutropenia due to the concurrent treatment of anti-cancer chemotherapy is also demonstrated in 100 patients. Preferably, the vancomycin resistant Enterococcus is selected from the group consisting of *E. avium, E. casseliflavus, E. durans, E faecalis* and *E. faecium*. More Preferably, the vancomycin resistant Enterococcus is selected from the group consisting of *E. avium, E. casseliflavus, E. durans* and *E. faecali*. More Preferably, the vancomycin resistant Enterococcus is selected from the group consisting of *E. durans, E. faecalis* and *E. faecium*. More Preferably, the vancomycin resistant Enterococcus is selected from the group consisting of *E. avium, E. faecalis* and *E. faecium*. More Preferably, the vancomycin resistant Enterococcus is selected from the group consisting of *E. faecalis* and *E. faecium*. Most preferably, the vancomycin resistant Enterococcus is *E. faecalis*.

Administration of the Fermented *Glycine max* (L.) Extract

In this invention, the fermented *Glycine max* (L.) extract may be administered alone or in a composition comprising the fermented *Glycine max* (L.) extract and a pharmaceutically acceptable carrier, diluent and/or excipient. Preferably, the fermented *Glycine max* (L.) extract is fermented soybean extract or fermented black soybean extract. The fermented *Glycine max* (L.) extract may be administered at a dose of about 0.001 to 40 ml/kg body weight, with a maximum dose of 2000 ml per person per administration. Preferably, the dose of the fermented *Glycine max* (L.) extract is 0.01 to 20 ml/kg, more preferably 0.1 to 5 ml/kg, body weight of the subject. These doses are based on the fermented *Glycine max* (L.) extract in the concentrated form, but appropriate doses of the fermented *Glycine max* (L.) extract in the unconcentrated form or dry powder form can be calculated accordingly. The dose can be adjusted based on the health condition of the subject or the disease to be prevented or treated.

The fermented *Glycine max* (L.) extract was demonstrated to be highly safe for daily intake of 1–10 ml on a long-term basis in a 6 months chronic toxicity study of rodents. Mice receiving a dose of 10 ml/kg and 1 ml/kg for 28 days did not exhibit any significant difference or abnormal symptom in a subacute oral toxicity study. No signs of gross toxicity or mortality were observed in two groups of tested animals administered 20 ml/kg and 1 ml/kg in an acute oral toxicity study of rodents. The fermented *Glycine max* (L.) extract was demonstrated to be non-mutagenic in Ames test, to not cause chromosomal damage in mammalian cells in vitro and to not induce micronuclei in bone marrow cells in ICR mice tested.

When the fermented *Glycine max* (L.) extract is administered in pregnant women, the dosage of the fermented *Glycine max* (L.) extract can be increased during pregnancy until the daily intake reaches 12 ml. The fermented *Glycine max* (L.) extract can be administered at early and midstage pregnancy, as well as delivery. The results showed that the fermented *Glycine max* (L.) extract could improve symptoms, including constipation, nausea, vomiting, and gastrointestinal discomfort, commonly found in pregnancy. In addition, the administration of the fermented *Glycine max* (L.) extract can reduce abnormalities during pregnancy and at delivery. The fermented *Glycine max* (L.) extract is not only good for health improvement during pregnancy, but it also produces no adverse effect as a long-term dietary supplement. Daily administration of the fermented *Glycine max* (L.) extract to newborns or infants daily increases weight gain of the babies or infants. Similarly, increased weight gain can be achieved in infants of nursing mothers continuously taking the fermented *Glycine max* (L.) extract.

The fermented *Glycine max* (L.) extract can also enhance hemopoeitic and liver functions after a surgical operation as demonstrated through daily administration of 1 ml of the fermented *Glycine max* (L.) extract along with other therapeutic products to women undergoing operation after hospital admission except for the surgery day and several post-surgery days.

This invention will now be described with reference to the following non-limiting examples.

EXAMPLE 1

LOX-15 is the main metabolizing enzyme in arachidonate acid (AA) metabolism. One of the metabolic pathways of AA involves 15-lipoxygenase, LOX-15, which leads to the formation of HETE (hydroxyeicosatetraenoic acid). HETE has been reported to play an important role in cancer cell metastasis. HETE can induce protein kinase C activity to result in cancer cell metastasis. HETE is also a mitogenic factor, which results in angiogenesis of cancer cells. LOX-15 was isolated from rabbit reticulocytes. Linoleic acid was used as a substrate of LOX-15 with or without the fermented soybean extract. The amount of HETE formed was determined spectrophotometrically. The data show that the fermented soybean extract had an inhibitory effect on LOX-15 (see FIG. 1). The result indicated that the fermented soybean extract inhibits angiogenesis and metastasis of cancer cells and induce apoptosis of cancer cells.

A further LOX-15 inhibition test was conducted according to the above-mentioned method to compare the inhibition efficacy of LOX-15 between the unfermented soybean and the fermented soybean extract. The results show that the inhibition efficacy of the fermented soybean extract was over four times of the unfermented soybean extract.

EXAMPLE 2

The fermented black soybean extract was tested in rabbit reticulocytes for the inhibitory effect on LOX-15. The test method refers to the method described in Analytical Biochemistry, 1992, 201, 375–380. The 1%, 0.5%, 0.1%, 0.05% and 0.01% (v/v) of black soybean extracts were used in incubating the reticulocytes at 4° C. for 10 minutes. The incubation buffer is 0.05 M potassium phosphate buffer (pH5.9). The resulting 13-HPODE is quantified by Spectrophotometer.

Figure 2:
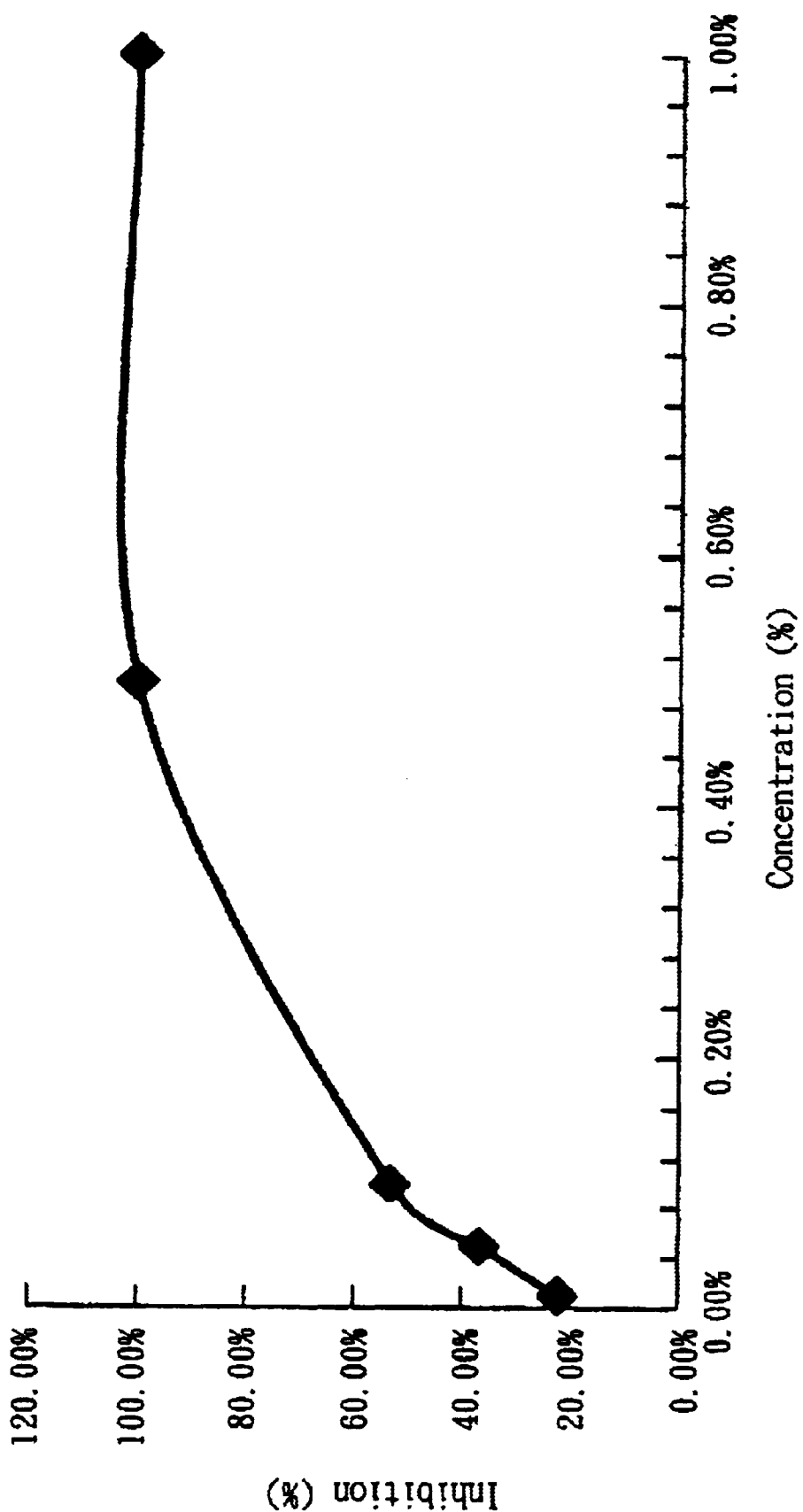
FIG. 2 shows the relation of the concentration of the black soybean and its inhibition rate to LOX-15.

The relation of the concentration of the black soybean and its inhibition rate to LOX-15 was shown in FIG. 2.

A further LOX-15 inhibition test was conducted according to the above-mentioned method to compare the inhibition efficacy of LOX-15 between the unfermented black soybean and the fermented black soybean extract. The LOX-15 inhibition rate of the unfermented black soybean was shown in below Table 1:

TABLE 1

| Unfermented Black Soybean (concentration, %) | LOX-15 Inhibition Rate (%) |
|---|---|
| 10 | 97.32 |
| 1.00 | 25.00 |

The LOX-15 inhibition rate of the fermented black soybean extract was shown in below Table 2:

TABLE 2

| Fermented black soybean extract (concentration, %) | LOX-15 Inhibition Rate (%) |
|---|---|
| 1.00 | 100.00 |
| 0.50 | 100.00 |
| 0.10 | 53.10 |
| 0.05 | 36.55 |
| 0.01 | 22.07 |

The results shown in the above tables show that the fermented black soybean extract has an unexpected superior efficacy in inhibiting LOX-15.

EXAMPLE 3

The fermented soybean extract functioned as an antioxidant and in the removal of free radicals. Several models published previously were used to study the antioxidant capacity of the fermented soybean extract, with Vitamin C and TroLOX used as positive controls. The following methods were used for determining the antioxidant activity: (1) NBT method (2) $H_2O_2$ reduction method (3) DPPH reduction (4) TRAP reduction method (5) Conjugated diene (6) Lipid peroxidation (7) Chemiluminescence (FIG. 3, FIG. 4, FIG. 5) in the presence of active oxygen. All results demonstrated that the fermented soybean extract has the highest antioxidant activity against unsaturated fatty acid and peroxidation compared with Vitamin C and TroLOX.

Figure 3A:
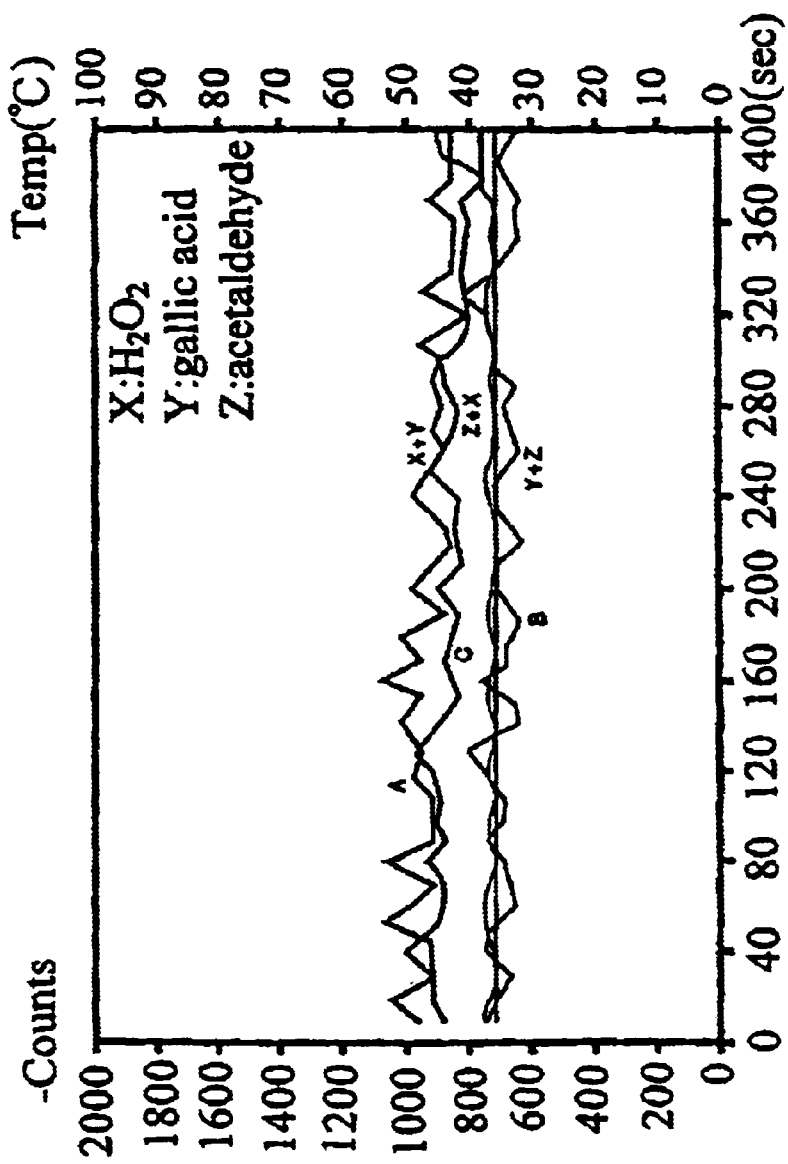
In FIG. 3(a), curve A refers to the chemiluminescence after the addition of X and Y together; curve B refers to the chemiluminescence after the addition of Y and Z together; and curve C refers to the chemiluminescence after the addition of X and Z together.
Figure 3B:
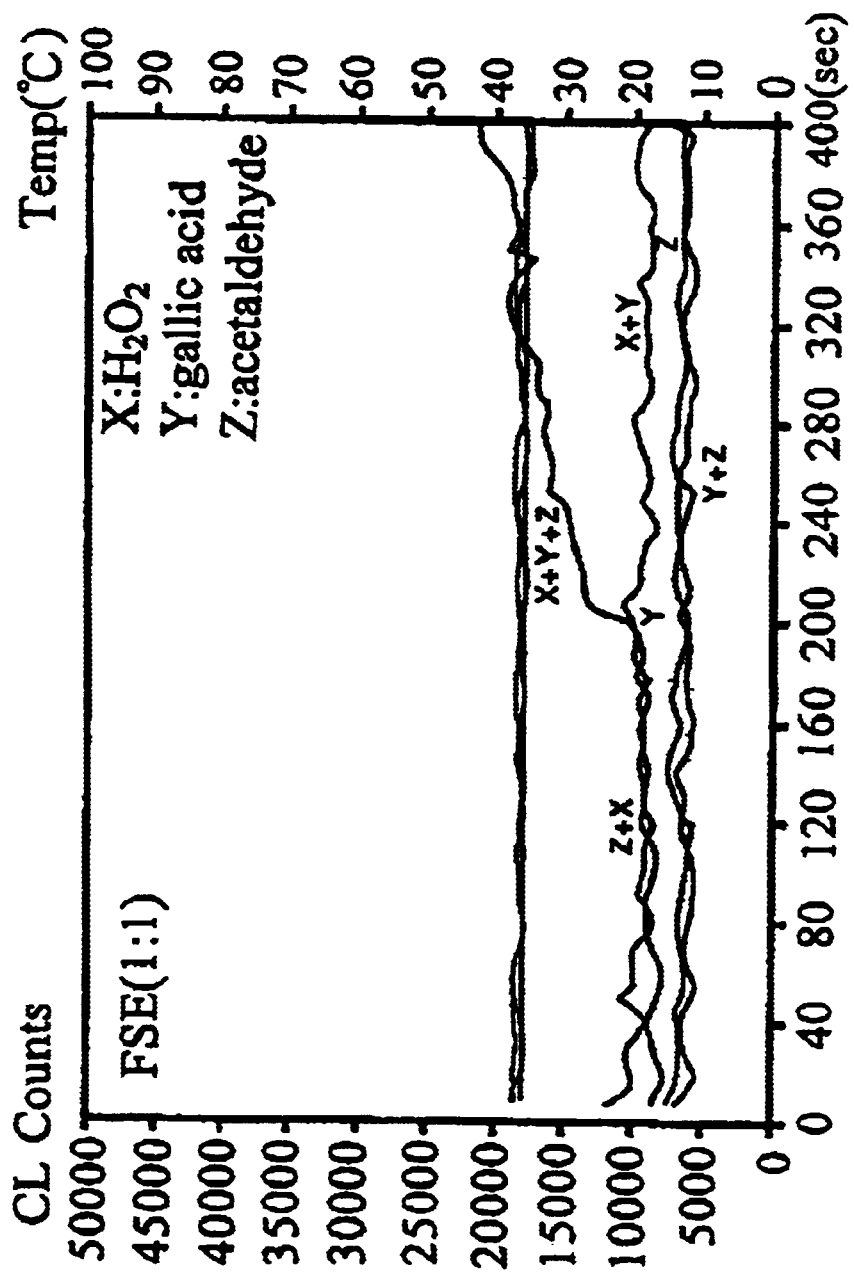
FIG. 3(b) shows that, when gallic acid was added into a mixture of X and Z at 200 seconds, the chemiluminescence was increased (i.e. the chemiluminescence occurred only in the presence of X, Y and Z all together).
Figure 4A:
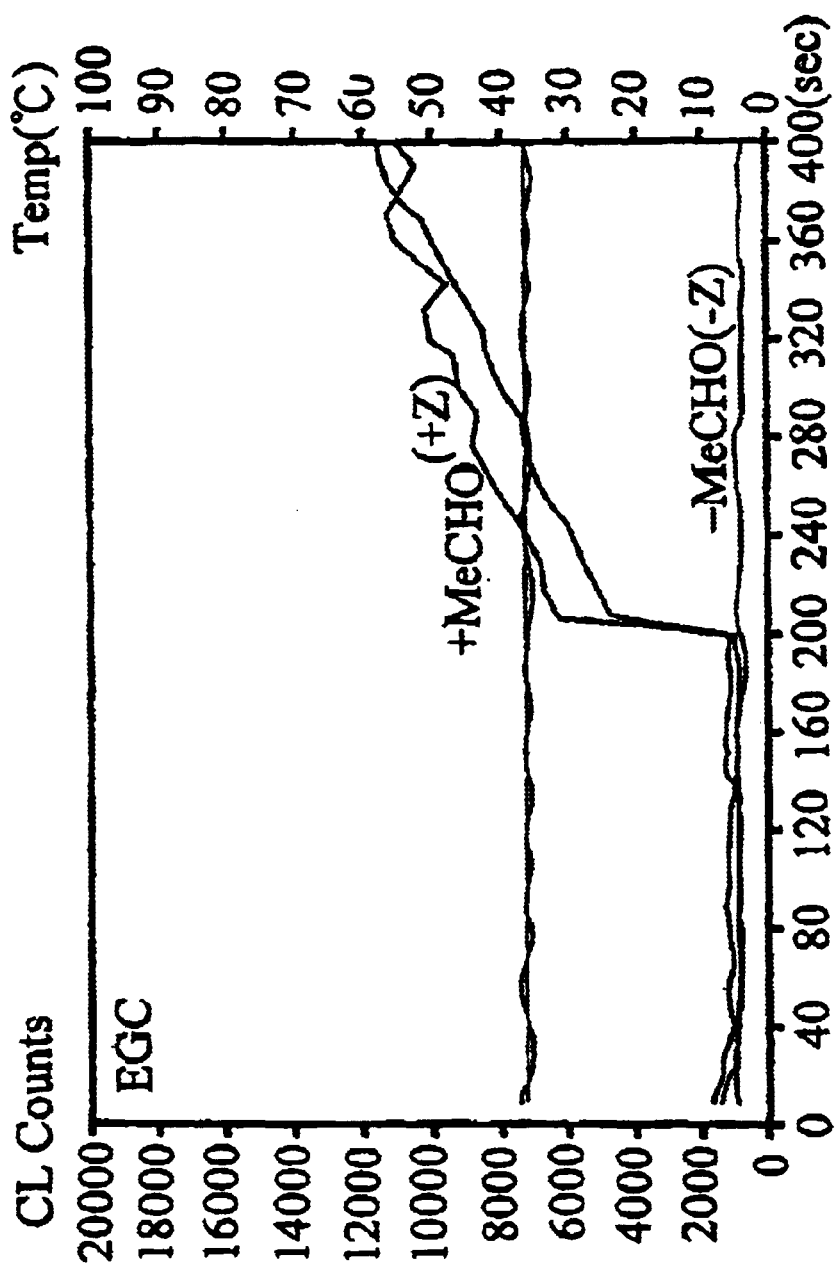
FIG. 4(a) shows the chemiluminescence determined with or without acetaldehyde when EGC, i.e. epigallocatechin which is a polyphenol, was added as the antioxidant at 200 seconds.
Figure 4B:
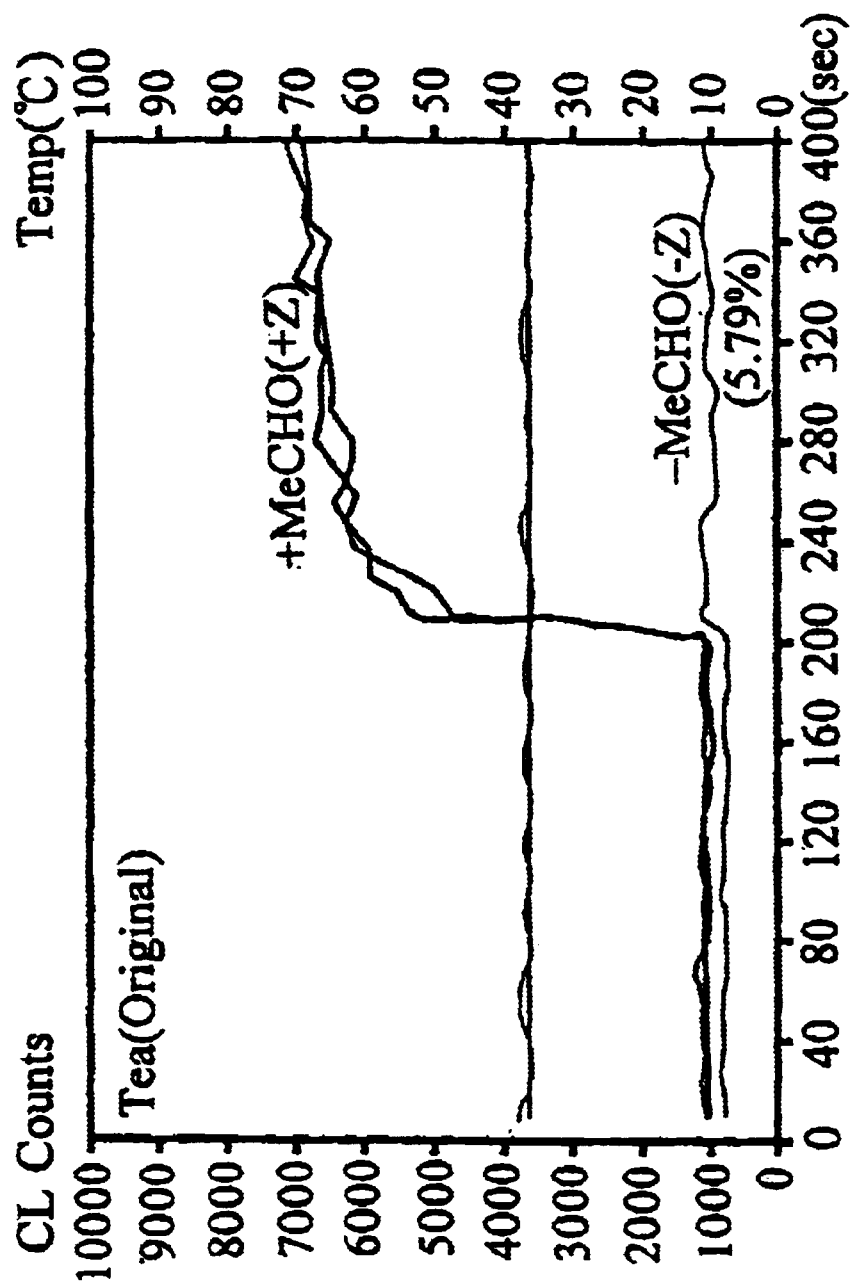
FIG. 4(b) shows that when tea was added as the antioxidant at 200 seconds, its chemiluminescence emitted in the absence of acetaldehyde (+Z) is 5.79% of that in the presence of acetaldehyde.
Figure 4C:
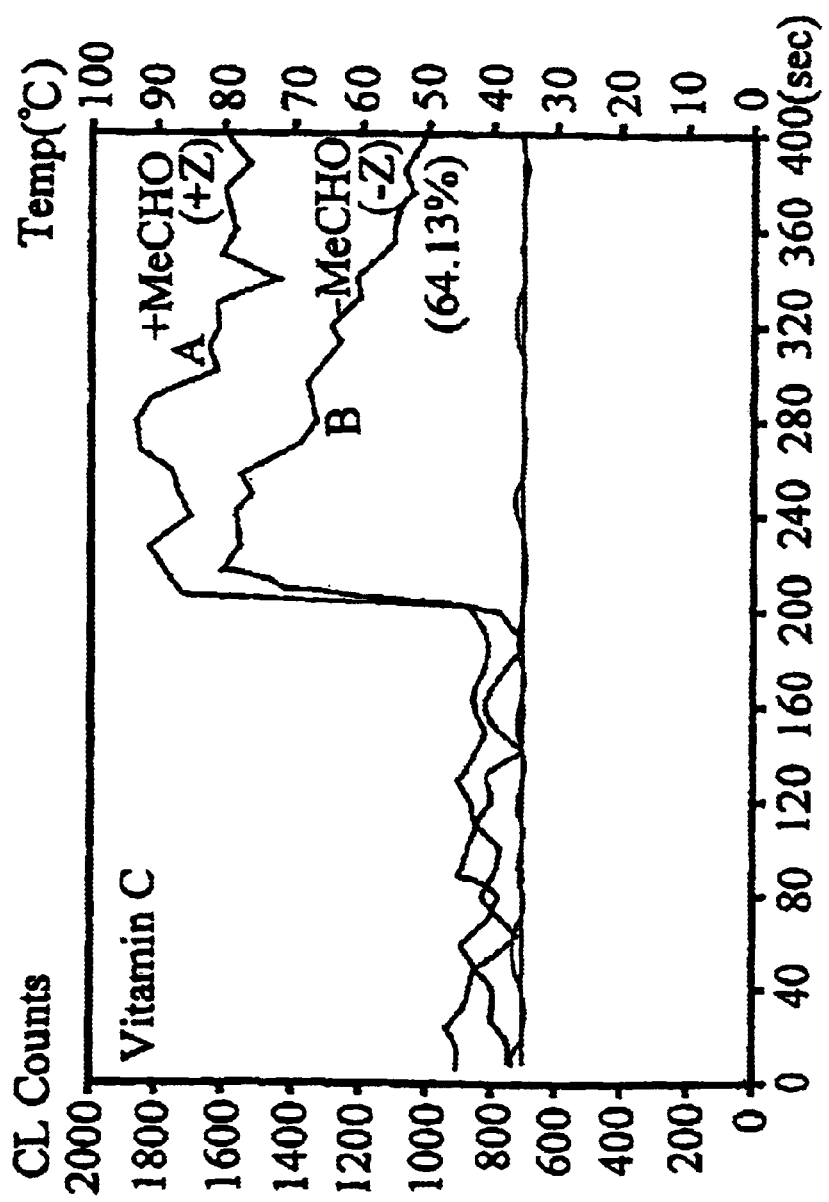
FIG. 4(c) shows that, when vitamin C was used as the antioxidant, the chemiluminescence intensity in the absence of acetaldehyde was 64.13% of that detected in the presence of acetaldehyde.
Figure 5A:
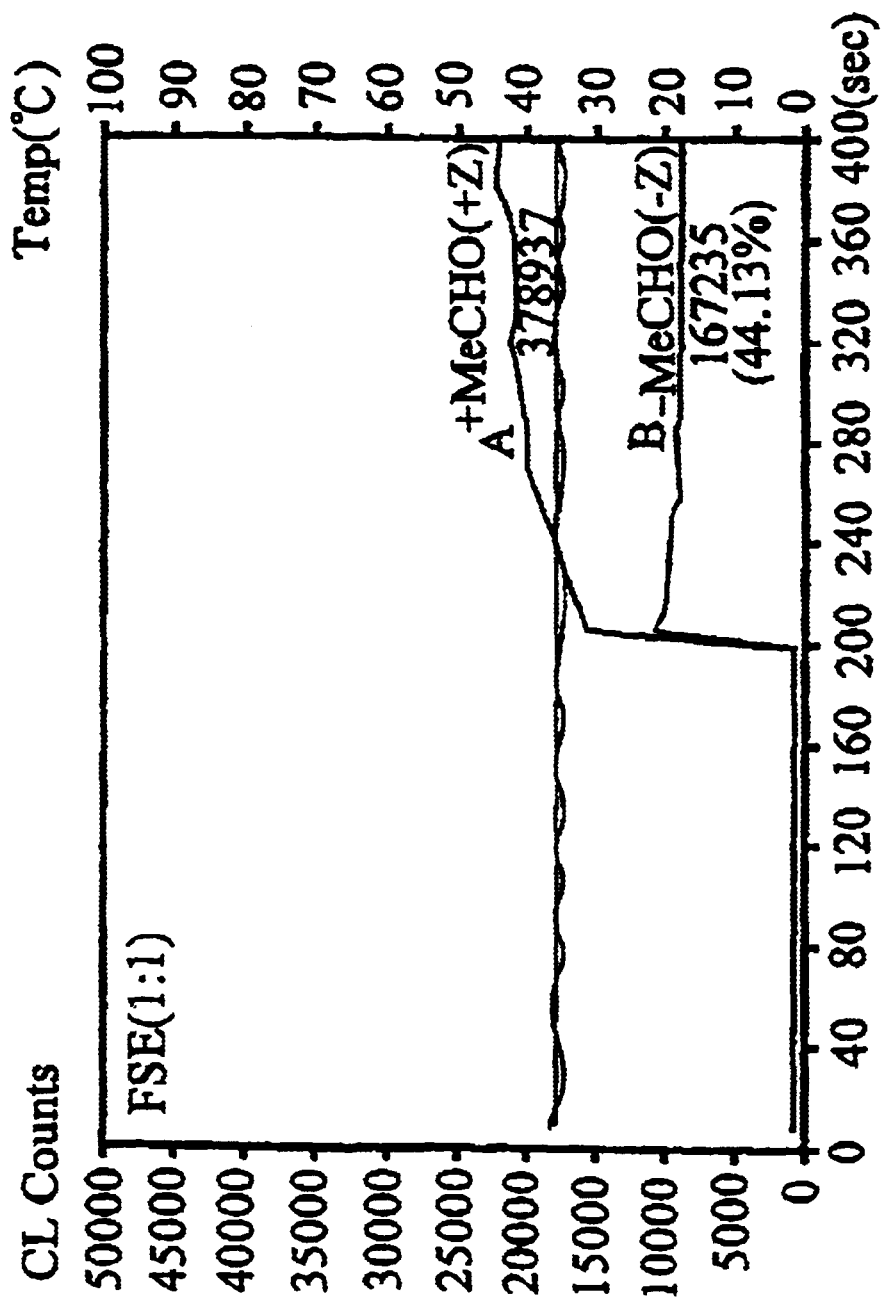
FIG. 5(a) shows that, at a FSE concentration of 1:1, the chemiluminescence intensity in the absence of acetaldehyde was 44.13% of that in the presence of acetaldehyde.
Figure 5B:
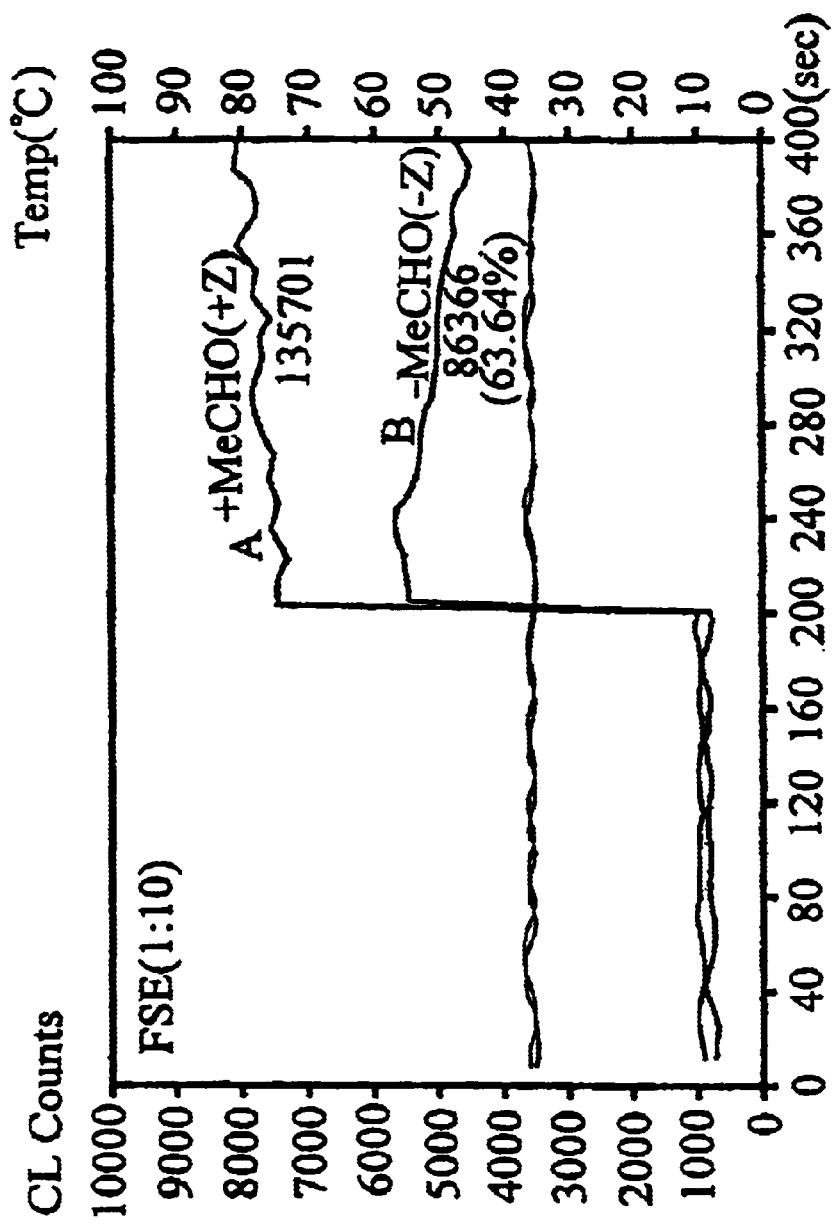
FIG. 5(b) shows that, at a FSE concentration of 1:10, the chemiluminescence intensity in the absence of acetaldehyde was 63.64% of that in the presence of acetaldehyde.
Figure 5C:
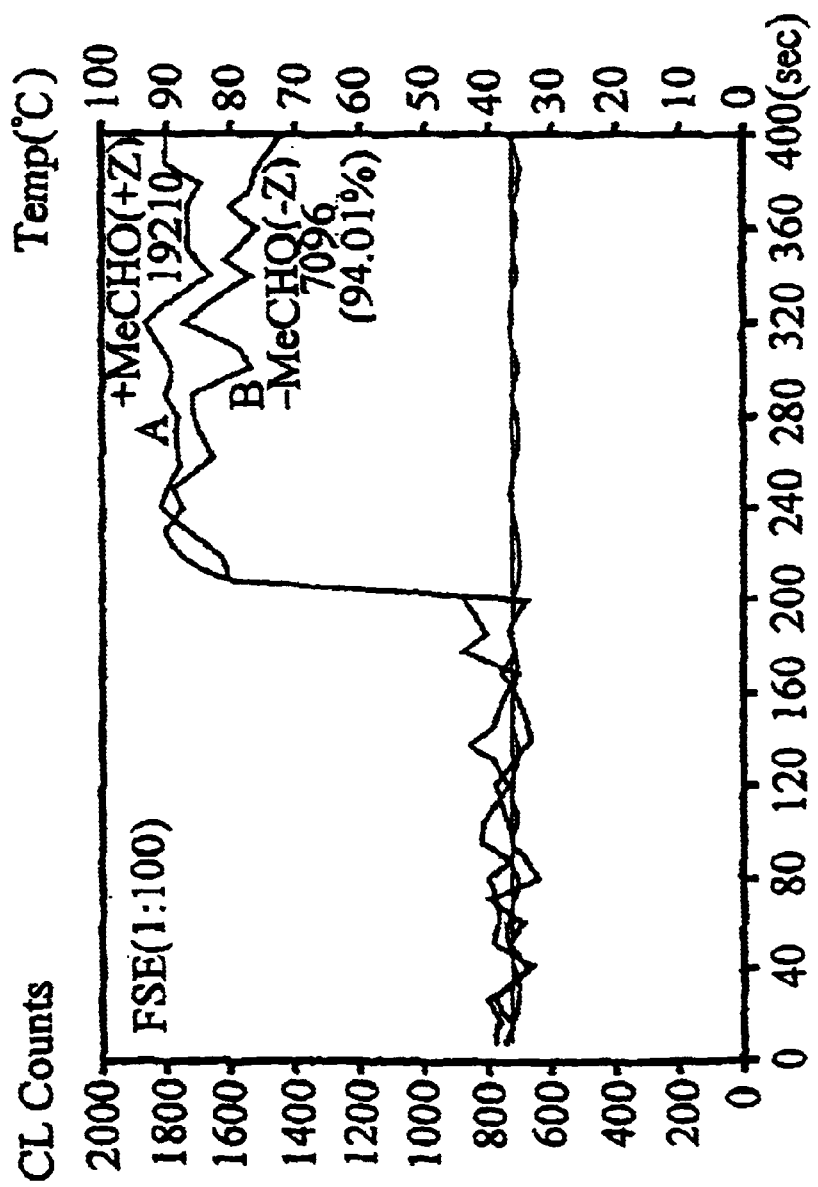
FIG. 5(c) and (d) show that, at a FSE concentration of 1:100 or 1:500, the chemiluminescence intensity in the absence of acetaldehyde was at least 90% of that in the presence of acetaldehyde.
Figure 5D:
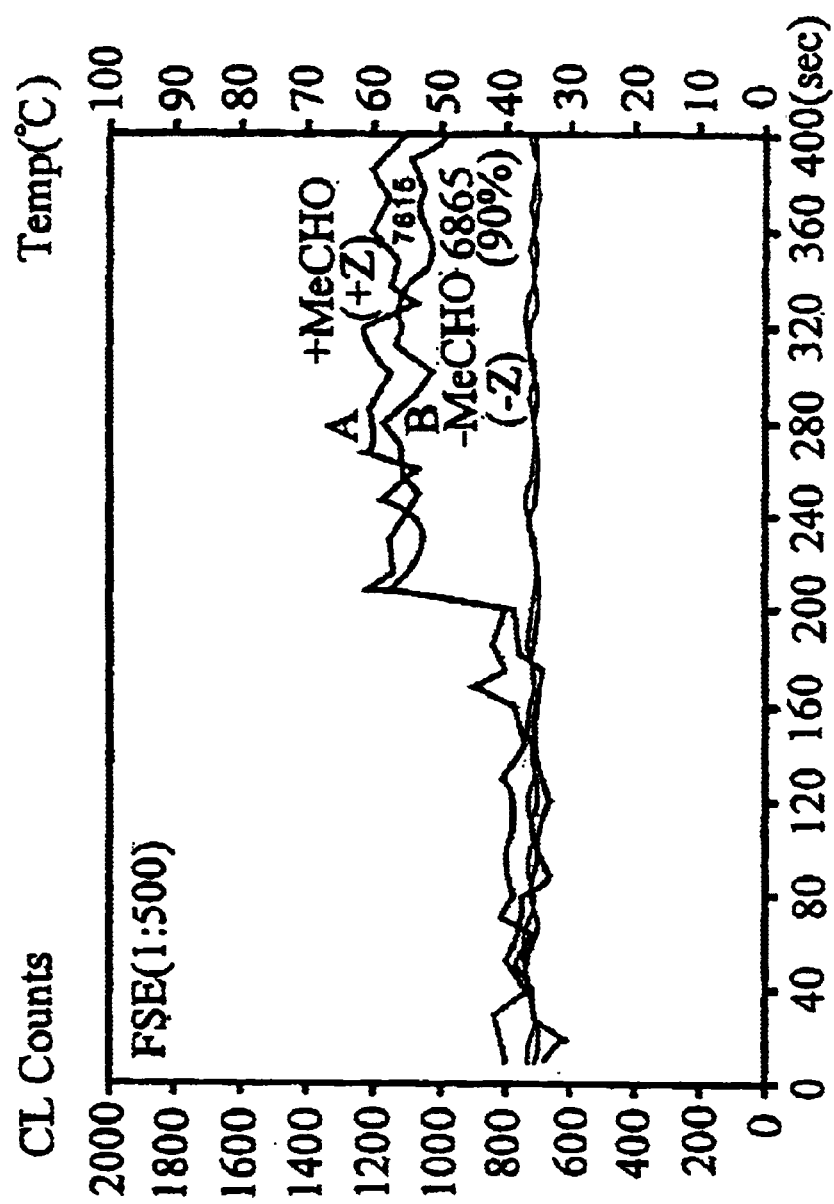
FIG. 5 shows the antioxidant effect of different concentrations of the fermented soybean extract, FSE. At a temperature of 37° C., with $H_2O_2$ used as a peroxide in the presence or absence of acetaldehyde as a radical receptor (Z), the chemiluminescence was measured and the fermented soybean extract at different concentrations was added at 200 seconds.

Experiments demonstrated that the fermented soybean extract functions both as a antioxidant and free radical acceptor in the Okubo test system for chemiluminescence acceptor in the presence of active oxygen. The experiments were performed by measuring chemiluminescence in a liquid of hydrogen peroxide with or without acetaldehyde. Known antioxidants, e.g. gallic acid (FIG. 3(b)), EGC, tea and vitamin C (FIGS. 4(a)–(c)) or the fermented soybean extract (FIG. 5) was added at 200 seconds. The data are shown in FIGS. 3–5. FIG. 3(b) shows that chemiluminescence was increased at 200 seconds when gallic acid was added to a mixture of hydrogen peroxide and acetaldehyde. FIG. 4 shows that when EGC, tea or vitamin C was added at 200 seconds, the chemiluminescence was increased when acetaldehyde was present. However, the chemiluminescence was also increased in the absence of acetaldehyde when vitamin C was added at 200 seconds (FIG. 4(c)) demonstrating that the anti-oxidant mechanism of vitamin C probably differs from that of EGC and tea. FIG. 5 shows that, after the addition of the fermented soybean extract at 200 seconds, the chemiluminescence increased indicating that the fermented soybean extract was a powerful anti-oxidant. The anti-oxidant activity of the fermented soybean extract means that the fermented soybean extract can function in removing free radicals. With anti-oxidant and free radical removing functions, the fermented soybean extract is useful in promoting the general health of individuals or improving the health of subjects in need of health improvement because oxidative stresses, such as excessive presence of reactive oxygen species and lipid peroxidation, are known to be harmful to the body.

EXAMPLE 4

Figure 6A:
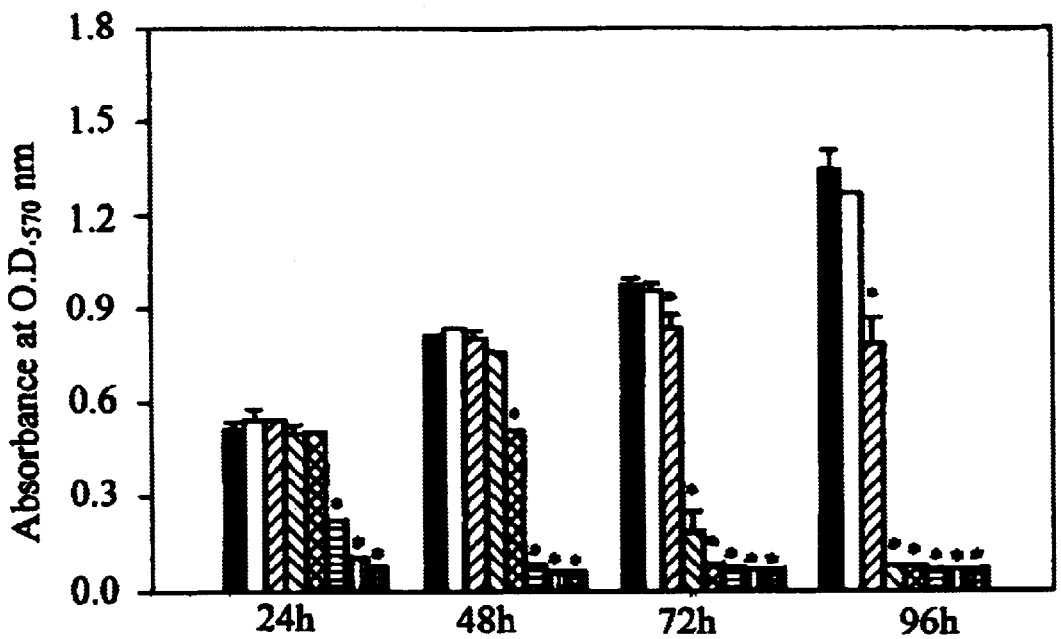
FIG. 6(A) shows the raw data from the MTT assay and FIG. 6(B) shows the percentage of cell viability. The cell viabilities after the FSE treatments were expressed with the absorbance of the control group at each time point taken as 100% in FIG. 6(B). Each bar represents the mean (n=3) □ standard errors. Unpaired student t test was used to determine the significant difference (*$p<0.05$).
Figure 6B:
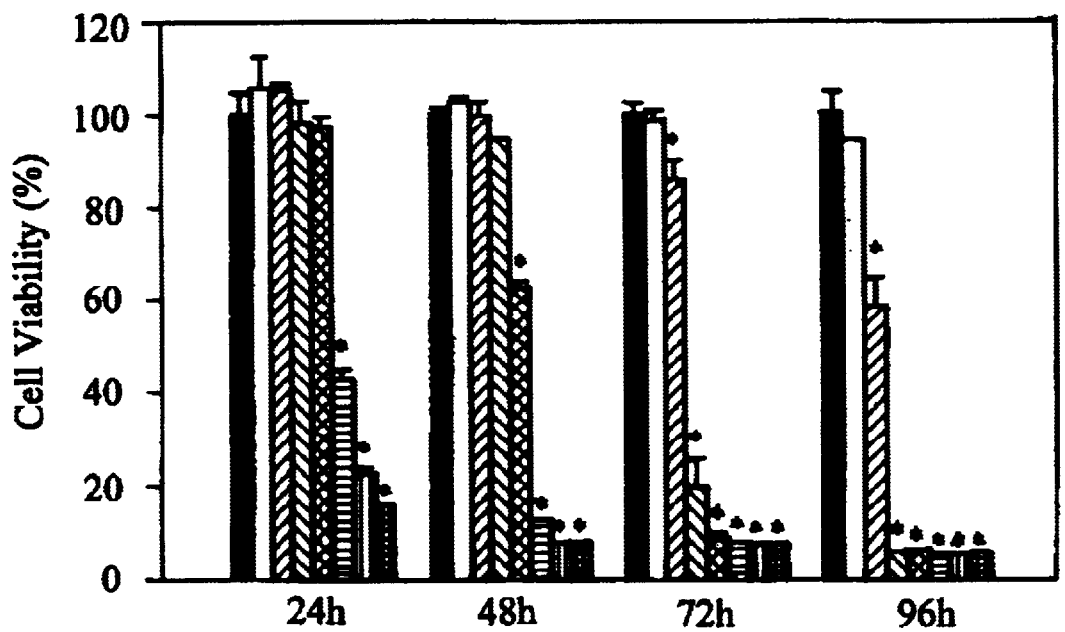

A human breast cancer cell line MCF-7 (ATCC HTB-22) was used to study the anti-cancer activity of the fermented soybean extract. The cytotoxic effects of the fermented soybean extract was demonstrated in the cancer cell line (see FIG. 6). Compared with the control group of each cell, the value of fermented soybean extract treatments was then normalized to refsect cell viability. The result showed that treatment with fermented soybean extract at various concentrations (0.8 mg/ml, 1.6 mg/ml, 3.2 mg/ml, 8 mg/ml, 16 mg/ml) for 48 hours caused significant reduction in the viability of MCF-7 cells.

Experiments conducted show that strong cytotoxic activities on breast (MCF7), lung (H460) and liver (Hep G2) cell lines were detected at low (0.8 mg/ml) concentration of the fermented soybean extract. Maximal cytotoxicities of cervix (HeLa) and lung (H1299) cancer cells were achieved at 3.2 mg/ml, whereas kidney (293) and colon (HT-29) cells were at 8 mg/ml. Among the cell lines tested, MCF-7 (breast cancer cell line) showed the most sensitive response.

Figure 7B:
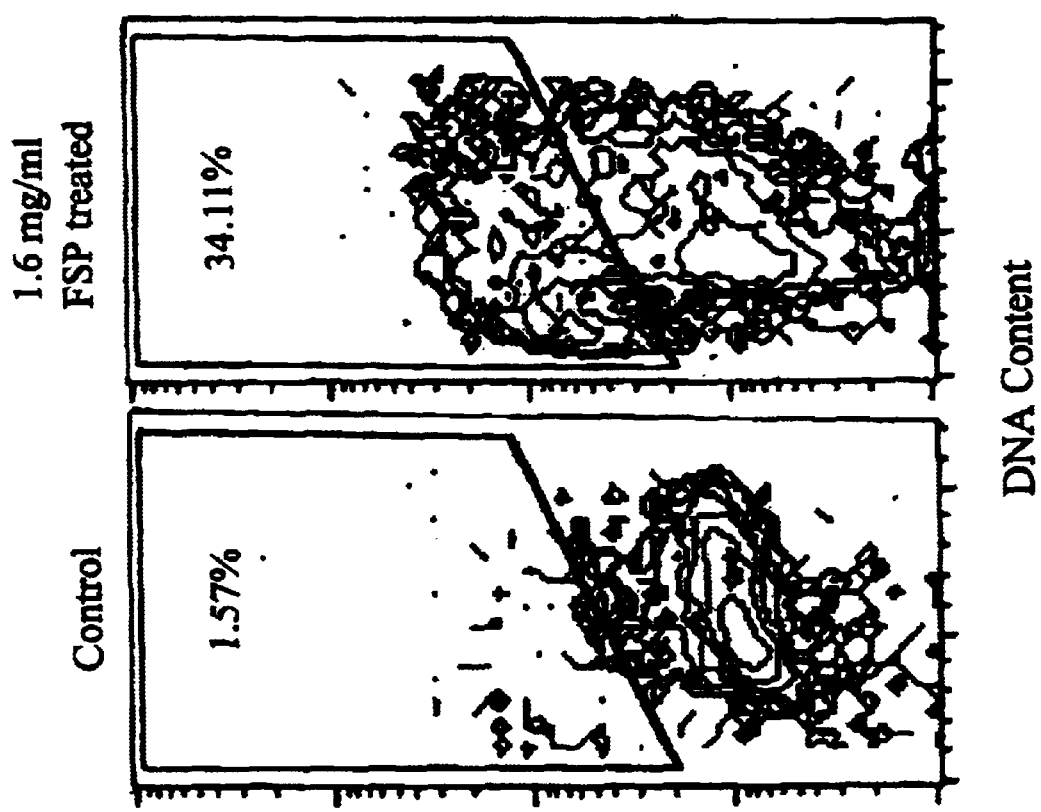
In FIG. 7(B), cells in the gated region were labeled with FITC-dUTP by TdT enzyme and were identified as cells that had undergone apoptosis. The result was from one experiment that is representative of three similar experiments.
Figure 7A:
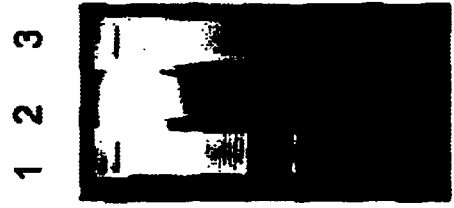
In FIG. 7(A), lane 1 represented the DNA marker; lanes 2 and 3 represented the control and FSE-treated MCF-7 cells, respectively.

Characterized by electrophoresis as well as quantified by TUNEL assay and flow cytometry, the fermented soybean extract was demonstrated to trigger apoptosis in MCF-7 cells (see FIG. 7). The apoptotic nuclei increased from 1.57% to 34.11% when the MCF-7 cells were treated with the fermented extract. The results demonstrated that the reduction of cell viability by fermented soybean extract was cause by a successfully triggering of apoptotic cell death, at least, in the case of MCF-7 cells.

EXAMPLE 5

Figure 8:
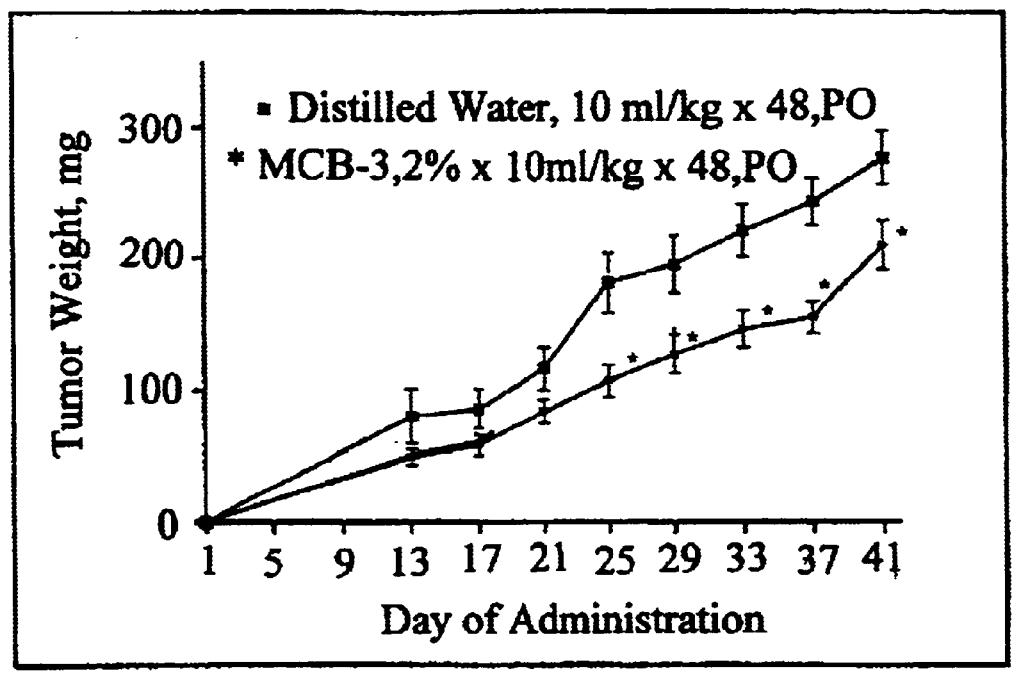
FIG. 8 shows the effect of administration of the fermented soybean extract (with a code name MCB-3) on the tumor weight in SCID mice implanted with MCF-7 cells in a xenograft experiment. The mean±standard error of each of the groups are presented in FIG. 8. Unpaired Student's T-test was used to compare the treatment groups with the control (the asterisks indicate significance at $p<0.05$).
Figure 9:
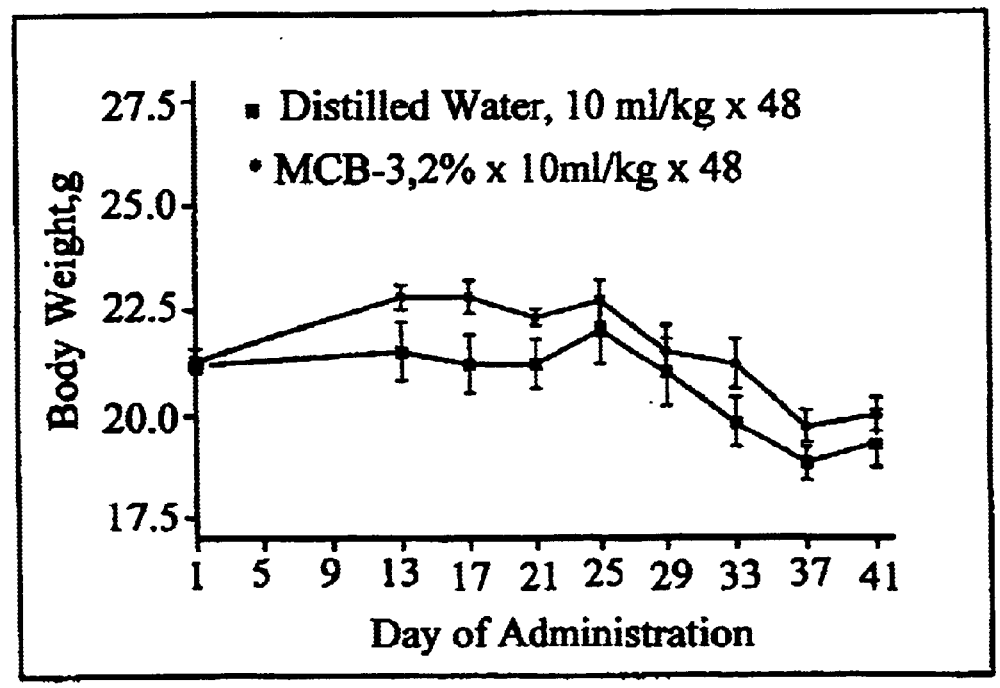
FIG. 9 shows the effect of administration of the fermented soybean extract on the body weight of SCID mice implanted with MCF-7 cells in the xenograft experiment. The mean±standard error of each of the groups are presented in FIG. 9. Unpaired Student's T-test was used to compare the treatment groups with the control (the asterisks indicate significance at $p<0.05$).

The fermented soybean extract was diluted with distilled water to make a 2% solution. Severe combined immune deficiency (SCID) female mice were transplanted with MCF-7 cells via a subcutaneous injection of $1 \times 10^7$ MCF-7 cells into the dorsal side of the mouse (this day was denoted as day 1). Estradiol benzoate was injected subcutaneously weekly at a dose of 50 ug/mouse for 4 weeks. The SCID mice were administered daily with a carrier or 2% fermented soybean extract by oral gavage in a dosing volume of 10 ml/kg body weight for 7 days before tumor cells implantation and then daily for 41 days after tumor cells implantation (the dose of 10 ml of the 2% solution per kg body weight was equivalent to a dose of 0.2 ml of the fermented soybean extract in the concentrated form per kg body weight). The tumor size, body weight, and the signs of overt animal toxicity after fermented soybean extract treatment were observed and recorded. According to the results obtained (see FIG. 8), the fermented soybean extract significantly inhibit the tumor growth from day 25 to day 41. Body weight of the tested animals did not have significant difference compared with the control group (see FIG. 9). No signs of overt animal toxicities were seen throughout the experiment. Daily oral intake of the fermented soybean extract was considered to have anti-tumor effects.

EXAMPLE 6

The anti-microbial activities of the fermented soybean extract were demonstrated by determining with in vitro methods. In the first experiment, *Salmonella typhimurium*, *Bacillus subtilis*, three strains (TMU-C74, TMU-D16 and TMU-E86) of *Helicobacter pylori* and vancomycin resistant *Enterococcus feacalis* were cultured in nutrient broth or BHI broth and transferred to Mueller Hinton agar plates or chocolate agar plates. The fermented soybean extract was put on a paper disk on the agar plate and the size of an inhibition zone was measured after incubation at 37° C. The data are shown in below Table 3:

TABLE 3

| Microbe | Fermented Soybean Extract | Inhibition Zone (mm) |
| --- | --- | --- |
| *Salmonella typhimurium* | Undiluted | 11 |
| *Bacillus subtilis* | Undiluted | 14 |
| *H. pylori* TMU-C74 | Undiluted | 15 |
| *H. pylori* TMU-D16 | Undiluted | 16 |
| *H. pylori* TMU-E86 | Undiluted | 15 |
| V.R. *E. feacalis* | Undiluted | 25 |
| V.R. *E. feacalis* | Diluted 50% | 15 |

In another experiment, the minimal inhibitory concentrations (MICs) of the fermented soybean extract were determined in *Salmonella typhimurium* (ATCC 14028), *Bacillus subtilis* (CRCC 10447), *Staphylococcus aureus* (ATCC 25923) and vancomycin resistant *Enterococcus feacalis*. Suspensions of these bacteria were adjusted to $3 \times 10^5$ CFU/ml. The adjusted bacteria suspensions were added to a 96-well plate with or without various concentrations, i.e. 10%, 5%, 2.5%, 1.25%, 0.65%, or 0.32%, of the fermented soybean extract. The plate was incubated at 37° C. for 15 hours. The MICs were determined after incubation and shown in below Table 4:

TABLE 4

| Microbe | MIC of Fermented Soybean Extract |
| --- | --- |
| *Salmonella typhimurium* | 2.5% |
| *Bacillus subtilis* | 2.5% |
| *Staphylococcus aureus* | 2.5% |
| V.R. *Enterococcus feacalis* | 1.25% |

The fermented black soybean extract was also used in testing the anti-microbial activities. The MICs were determined and shown in below Table 5:

TABLE 5

| Microbe | MIC of Fermented Black Soybean Extract |
| --- | --- |
| *Pseudomonas aeruginosa* | 3.125% |
| KP (*Klebsiella pneumoniae*) | 3.125% |
| M.R *Staphylococcus aureus* | 1.563% |

EXAMPLE 7

The effects of the fermented soybean extract on immunity modulation were studied.

(A) In Vitro Studies:

Spleen Cell Proliferation Assay (MTT Method).

Spleen cells were isolated from mice and put in a culture flask at $2 \times 10^6$ cells/ml in a RPMI medium with or without one of several mitogens, i.e. lipopolysaccharide (LPS), concavalin A (Con A) and phytohemagglutinin (PHA). The spleen cell cultures were incubated overnight for MTT assay. A sub-optimal concentration of 5 ug/ml of LPS combined with the fermented soybean extract at 1%, 0.5%, 0.1%, 0.05% or 0.01%, had no effect on spleen cell proliferation, especially for B cells. A concentration of 5 ug/ml of PHA combined with 0.05% of the fermented soybean extract increased the spleen cell number, especially for T cells, which was 2.32 fold of the spleen cell number obtained with PHA alone. According to this result, the fermented soybean extract has an effect on T and B cell interaction in immunity modulation. A concentration of 5 ug/ml of Con A combined with 0.05% of the fermented soybean extract produced a spleen cell number which was about 20% less than the spleen cell number obtained with Con A alone. According to this result, the fermented soybean extract could play a role in anti-inflammation reactions.

Macrophage Activity Assay.

Balb/c mice were injected with thiogllate. Three to four days after the injection, macrophages were isolated from the peritoneal cavity of the mouse and incubated with or without the fermented soybean extract at 37° C. for 30 minutes. *E. coli* cells conjugated with a fluorescence probe were added to the macrophage suspension and incubated at 37° C. for 2 hours. A phagocytosis assay was conducted with flow cytometry. The data showed that the fermented soybean extract at 0.05% enhanced the phagocytosis activity of the macrophage by about 71% compared with macrophages not treated with the fermented soybean extract.

(B) In Vivo Studies

Male ICR albino mice were injected intraperitoneally with vehicle, 0.8 ml of 1% of the fermented soybean extract per mouse, 0.8 ml of 0.1% of the fermented soybean extract per mouse, Levamisole at 30 mg/kg, or azimexone at 100 mg/kg. One hour after the intraperitoneal injection, *Candida albican* (ATCC 10231) was injected intravenously into the mouse at 1.5 to $2 \times 10^7$ CFU per mouse. The mortality of the mouse was determined daily for 10 days (see Table 6).

As shown in Table 6, the fermented soybean extract reduced the mortality of *Candida albican* in the mouse. The mortality reductive effect of the fermented soybean extract was more pronounced than that of levamisole.

Male ICR albino mice were pretreated with cyclophosphamide at 30 mg/kg on days 5, 3 and 1 before injected intravenously with *Candida albican*. On days 6, 4 and 2 before the intravenous injection of *Candida albican*, the mouse was treated with vehicle, 0.1% of the fermented soybean extract, 1% of the fermented soybean extract or azimexone at 100 mg/kg. The mortality of the mouse was determined daily for 10 days (see Table 7). As shown in Table 7, with cyclophosphamide pretreatment, the fermented soybean extract reduced the mortality of *Candida albican* in the mouse. The mortality reductive effect of the fermented soybean extract was comparable to that of azimexone.

Information as herein shown and described in detail is fully capable of attaining the above-described object of the invention, the presently preferred embodiment of the invention, and is, thus, representative of the subject matter which is broadly contemplated by the present invention. The scope of the present invention fully encompasses other embodiments which may become obvious to those skilled in the art, and is to be limited, accordingly, by nothing other than the appended claims, wherein reference to an element in the singular is not intended to mean "one and only one" unless explicitly so stated, bu rather "one or more". All structural and functional equivalents to the elements of the above-described preferred embodiment and additional embodiments that are known to those of ordinary skill in the art are hereby expressly incorporated by reference and are intended to be encompassed by the present claims.

Moreover, no requirement exists for an apparatus, a composition of matter, a device, or a method to address each and every problem sought to be resolved by the present invention, for such to be encompassed by the present claims. Furthermore, no element, component, or method step in the present disclosure is intended to be dedicated to the public regardless of whether the element, component, or method step is explicitly recited in the claims. However, it should be readily apparent to those of ordinary skill in the art that various changes and modifications in form, material, and fabrication material detail may be made without departing from the spirit and scope of the inventions as set forth in the appended claims. No claim herein is to be construed under the provisions of 35 U.S.C. §112, sixth paragraph, unless the element is expressly recited using the phrase "means for."

What is claimed is:

1. A method of inhibiting 15-lipoxygenase in a subject in need thereof, comprising administering about 0.001 to 40 ml/kg body weight of a fermented *Glycine max* (L.) extract to the subject, wherein the fermented *Glycine max* (L.) extract is prepared by fermenting an aqueous *Glycine max* (L.) extract with at least one lactic acid bacteria together with at least one yeast, wherein the inhibition of 15-lipoxygenase is used in treating or reducing the risk of cardiovascular disease.

2. The method of claim 1, wherein the *Glycine max* (L.) is black soybean.

3. The method of claim 1, wherein the lactic acid bacteria is a Lactobacillus species.

4. The method of claim 1, wherein the yeast is a Saccharomyces species.

5. The method of claim 1, wherein said cardiovascular disease is atherosclearosis.

* * * * *

UNITED STATES PATENT AND TRADEMARK OFFICE
CERTIFICATE OF CORRECTION

PATENT NO. : 6,685,973 B1
DATED : February 3, 2004
INVENTOR(S) : William Lu Kung-Ming It is certified that error appears in the above-identified patent and that said Letters Patent is hereby corrected as shown below:

Column 3,
Line 14, delete "5 X 104/ell" and replace with -- 5 x 104/cell --.

Column 4,
Lines 2 and 3, delete "Process for Producing the Fermented Soybean Extract" and insert same as title to section beginning in column 4, line 5.

Column 6,
Line 67, delete "atherosclearosis" and replace with -- atherosclerosis --.

Column 7,
Line 9, delete "lipopolysachrride" and replace with -- lipopolysacharride --.

Column 8,
Line 43, please delete "E. faecali" and replace with -- E. faecalis --.

Column 14,
Line 2, delete "atherosclearosis" and replace with -- atherosclerosis --.

Signed and Sealed this

Sixth Day of July, 2004

JON W. DUDAS
*Acting Director of the United States Patent and Trademark Office*